United States Patent [19]

Chuhran

[11] Patent Number: 6,136,340
[45] Date of Patent: Oct. 24, 2000

[54] FOOD ENERGY INHIBITOR FOR RODENTS

[76] Inventor: James E. Chuhran, 7676 Dolphin, Detroit, Mich. 48239

[21] Appl. No.: 09/197,548

[22] Filed: Nov. 23, 1998

Related U.S. Application Data

[63] Continuation-in-part of application No. 08/661,079, Jun. 10, 1996, which is a continuation-in-part of application No. 08/500,613, Jul. 11, 1995, abandoned.

[51] Int. Cl.⁷ ............................. A01N 25/00; A01N 25/34
[52] U.S. Cl. ......................... 424/439; 424/84; 424/403; 424/405; 424/408; 424/409; 424/410
[58] Field of Search ............................. 424/84, 403, 405, 424/408, 409, 410, 439; 514/951

[56] References Cited

U.S. PATENT DOCUMENTS

| | | |
|---|---|---|
| 1,952,977 | 3/1934 | Edmonds . |
| 4,287,183 | 9/1981 | Hagerman et al. ...................... 424/157 |
| 4,379,139 | 4/1983 | Dawson ..................................... 424/84 |
| 4,518,580 | 5/1985 | Pasarela ..................................... 424/16 |
| 4,581,378 | 4/1986 | Lazar ....................................... 514/681 |
| 4,815,923 | 3/1989 | Lush ........................................ 424/410 |
| 5,019,564 | 5/1991 | Lowe et al. ................................ 514/75 |
| 5,132,321 | 7/1992 | Corey ....................................... 514/457 |
| 5,290,556 | 3/1994 | McKibben et al. ..................... 424/405 |

*Primary Examiner*—Thurman K. Page
*Assistant Examiner*—S. Howard
*Attorney, Agent, or Firm*—Charles W. Chandler

[57] ABSTRACT

A food energy inhibitor for controlling rodents, such as rats and mice, comprises pellets of either crushed or dried corncobs, or, spent grain bound together with an attractant, such as molasses.

11 Claims, No Drawings

FOOD ENERGY INHIBITOR FOR RODENTS

CROSS-REFERENCE TO RELATED APPLICATION

This application is a continuation-in-part of application Ser. No. 08/661,079 filed Jun. 10, 1996 for "Toxicant-Free Rodent Exterminator", which in turn was a continuation-in-part of application Ser. No. 08/500,613, filed Jul. 11, 1995, for "Toxicant-Free Rodent Exterminator", now abandoned.

BACKGROUND OF THE INVENTION

Many products are available for controlling rodents, such as rats and mice, and insects, such as ants. Such products usually employ an inert substance combined with a rodenticide. However, products with a toxicant may only be used in carefully selected areas to avoid contaminating food supplies, water supplies, domestic animals and people. Further, products using a rodenticide are undesirable because an animal, bird, or reptile feeding on a poisoned rat or mouse may also die from the toxic product. As used in this specification, the word "toxicant" is intended to mean a poisonous additive.

Examples of such prior art products can be found in the following: U.S. Pat. No. 1,952,977 which was issued Mar. 27, 1934 to J. Bernard Edmonds for "Method of Treating Red Squill for Use as a Rodent Exterminator"; U.S. Pat. No. 4,287,183 which was issued Sep. 1, 1981 to John D. Hagerman and Brenda M. Hagerman for "Method for Killing Rodents"; U.S. Pat. No. 4,379,139 which was issued Apr. 5, 1983 to Ray F. Dawson for "Anticoagulant Rodenticide With Laceration Means"; U.S. Pat. No. 4,518,580 which was issued May 21, 1985 to Nunzio R. Pasarela for "Expanded Corncob Grits Having Increased Absorptivity and a Method for the Preparation thereof; U.S. Pat. No. 4,581,378 which was issued Apr. 8, 1986 to Remus Lazar and Emil P. Lira for "Rodenticide Compositions Comprising an Artificial Sweetener and a Rodenticide"; U.S. Pat. No. 4,815,923 which was issued Mar. 28, 1989 to Raymon W. Lush for "Sweet Corn Based Rodenticide"; U.S. Pat. No. 5,019,564 which was issued May 28, 1991 to H. Edward Lowe, Ricky L. Yoder and Clayton C. Nelson for "Non-Clay Agricultural Granule"; U.S. Pat. No. 5,132,321 which was issued Jul. 21, 1992 to Garland G. Corey for "Anticoagulant/Surfactant Rodenticidal Compositions and Method"; and U.S. Pat. No. 5,290,556 which was issued Mar. 1, 1994 to Gerald H. McKibben, Joseph C. Dickens and James W. Smith for "Plastic Bait Composition for Attracting and Killing Crop Pests".

Some non-toxic bait compositions have been disclosed in the prior art. These include U.S. Pat. No. 5,186,935 which was issued Feb. 16, 1993 to John W. Tucker for "Insecticidal Bait Composition and Method of Making Same".

SUMMARY OF THE INVENTION

The preferred embodiment of the invention is a cellulose product used for controlling rodents without using a toxic component. It includes an active ingredient and an attractant/binder. The rodents receive no nourishment from the cellulose and die from lack of energy. The formula of the preferred product is:

| Material | Percentage | Purpose |
| --- | --- | --- |
| Cellulose | 99% | Active Ingredient |
| Molasses | 1% | Attractant/Binder |

Cellulose

Definition

The major component of the food energy inhibitor; chief constituent of the cell wall of plants, wood, hemp, paper, etc., a carbohydrate.

| Types of Cellulose: | Corn Cob | Wheat |
| --- | --- | --- |
| | Peanut Shells | Bagasse |
| | Hops | Bran |
| | Beet Pulp | Barley |
| | Rice Germ | Whole Oats/Oat Bran |
| | Rye | Buckwheat |

Molasses is used as an attractant/binder because, after reviewing the literature, many attractants also provide binding capability. For example, cane molasses is used extensively in the baking industry as a shortening agent. It improves the flavor, provides cohesion and improves the "texture" of the foodstuff.

Binder

Definition

An agent used to improve the consistency, cohesiveness, and texture of the preferred food energy inhibitor, a substance to improve the palatability of the food energy inhibitor to rodents.

General Category

Fats, Oils, Protiens

| Examples: | Peanut Oil | Soybean Oil |
| --- | --- | --- |
| | Cottonseed Oil | Corn Oil |
| | Vegetable Oil | Coconut Oil |
| | Gluten | Lard |
| | Tallow | Nut Butter (i.e. peanut) |

Oils are used extensively as shortening; in salad oils, livestock feed, soaps, paints and lubricants. Glutens are proteins derived from grains; used in the preparation of foods, especially cereals; used in cattle feed and in making adhesives.

Attractant

Definition

A substance used to attract pests such as rodents to the bait. The purpose of the attractant is to overcome "bait shyness" and encourage the consumption of the food energy inhibitor.

Rodents are by nature neophoebic and therefore, shy to try new foods or explore objects that they have not been associated with in the past. Therefore, the attractant and binder may work in conjunction or synergistically to enhance the palatability of the product, which allows the rodent to eat until replete, and because it does not gain energy from the cellulose, subsequently death occurs.

General Category

Simple sugars, Complex carbohydrates, Proteins

| Examples: | Maple Sugar | Beet Molasses |
|---|---|---|
| | Cottonseed Meal | Cane Molasses |
| | Cane Syrup | Honey |
| | Corn Syrup | Bone Meal |
| | Malt Sugar | Beer/Ales |

Cane molasses is used extensively in baked goods and candies and is a major raw material for livestock feed and as a binder. Cane syrup and corn syrup are used extensively in baked goods, candies act as binders.

Blood products may or may not enhance the attractiveness of the bait to the rodent. Rodents prefer protein, grains and sugars. However, blood proteins do exist.

The mechanism of action for the food energy inhibitor is to encourage the rodent to consume the product (the purpose of the attractant) while preventing the absorption of food from the gut of the rodent. Grains are the seed-like fruit of certain species of the grass family such as rice, wheat, corn, oats, barley, and rye. The plants that produce these fruits are also called grains.

Using corn as an example, the corn plant is actually a grass and the kernels themselves are grains. The fiber in corn is soluble; yet, oats and barley, which are in the same species as corn, contain fiber that is soluble. The fiber in corn passes through the GI tract unchanged where the fiber in oats and bran are affected. The solubility of the grain used in the food energy inhibitor can effect efficacy.

The use of these materials in their respective categories is well documented and therefore, further testing is unnecessary.

Many factors affect the efficacy of products used to control pests. For instance, rodents do not possess the morphological or physiological mechanism to regurgitate food as do dogs, cats and other animals. This is one reason why rodents are so susceptible to poisons. The key, however, is not the poison but the attractiveness/palatability of the bait. If you can get the rodents to eat bait with a toxic substance, and they only consume enough to get sick, they will not eat the bait again and become what is known as "bait shyness".

However, if the rodents continue to consume a non-nutritional substance (cellulose), their energy level puts them in a "rodent coma", without the use of a primary or secondary active toxic.

The preferred embodiment of the invention comprises pellets formed of crushed spent grain such as corncobs, and a rodent attractant such as molasses, which also functions as a binder.

Another object of the invention is to provide a toxicant-free product for controlling insects, such as ants, in the form of pulverized or ground-up spent grain such as corncobs that are dried and sprinkled in the area where the ants are present.

Some advantages of the invention are that the product can be safely used indoors, outdoors, in the home, around food and in the fields. Airplanes, helicopters, and other forms of vehicles can apply it.

In one form of the invention, the material will not dissolve in water. The product can be dispensed by hand without fear of toxic chemical exposure. It is completely non-toxic to other animals, such as birds, cats, dogs, or reptiles that might eat a rat or mouse killed by the product. The product will not contaminate a drinking water supply, will not harm fish, birds or wild life, will not cause any harmful effects if swallowed or absorbed through the skin, will not harm children or pets, and can be safely eaten by domestic animals and livestock.

In the preferred form of the invention, the product is applied as a pellet. Tests indicate that the product is selective because it is not harmful to animals, other than rats and mice.

The grain is milled to separate the floury endosperm from the bran and germ. The milled grain is then rolled to extract the oil from the germ. The remaining product is a non-nutritional by-product known in the industry as "spent grain."

The spent grain is then passed through a drying process and aerated to achieve a moisture content ranging from 7%–9%. Another rolling and aeration process using double rollers removes any remaining colloidal minerals to produce all natural cellulose.

The cellulose in a workable size particle is then mixed with the attractant and binding substance and pelletized to ¼ to ⅜ inch in length.

The product is dried to a moisture level of preferably 7%–9%, which causes the product to absorb the moisture from any existing food in the gut of the rodent.

The attractant is selected according to what is readily available and what the rodents are accustomed to eating. It may range from molasses, beer, blood, shrimp, nuts, fish, beets, dry or liquid.

The pellets may be used in both urban and rural settings, around buildings, including homes, in agricultural settings, such as barns, grain bins, and animal quarters.

DESCRIPTION OF THE PREFERRED EMBODIMENT

The preferred composition is produced by preparing a substantially dry base of a cellulose such as crushed corncobs, without kernels, and 1% by weight of molasses as a rodent attractant and binder. The kernels are first removed from the corncobs in a mill. The core of the corncobs is then drilled to recover a powder used for other purposes. The remaining rings are crushed to a U.S. sieve size of 20–40 so as to be easily ingested by the rodent.

The crushed corncobs are dried to a 7%–9% level of moisture, by weight. The dried particles are then mixed with molasses in a ribbon mixer. Some steam is applied to caramelize the molasses. The mixture is formed into pellets in a pelletizing mill, such as a Scott Pellet Mill. The molasses acts both as a binder and a sweet attractant. Preferably, the pellets are about 3/15", in diameter and typically ½" long.

The pellets are distributed in locations where the rats or mice are active. Over a period of several days, the rats and mice die after consuming the pellets.

When the corncobs are crushed in a finer powder-like form with or without an attractant, the powder can be distributed in the vicinity where ants are present. Tests indicate that the dried cellulose powder, without the attractant, is effective on such ants as carpenter ants, fire ants and termites. The material is spread around the ant hill so as to be in the ants' path. The ants die upon ingesting the powder.

The material used for rodents can be formed into shapes, other than pellets. Further, other sweets and attractants can be used, such as honey, chocolate, blood plasma, peanut butter, fish, beer and other similar materials.

The pellets may be coated with a paraffin or other coating to protect the composition from contact with water.

The pellets are placed in areas where evidence of rodent activity exists. The pellets are replenished as needed until signs of rodent activity ceases. For example for Norway rats: use 2 oz. (57 grams) every 15–30 feet of runways/walls. The pellets may also be placed directly in the burrows. For house mice, use no more than 2 oz. (57 grams) per 20 feet of runways/walls areas. Feeding vertically in ceilings and walls where rodents may have nesting sites is recommended for serious mouse infestation. The following examples illustrate the use of the preferred embodiment of the invention.

EXAMPLE I

Summary

Five male and five female Sprague Dawley derived rats were fed test molasses pellets. All animals died by day 7. Clinical observations included dehydration, tremors, lethargy, soft light stool and weight loss.

Purpose

To determine the effectiveness of the test material prepared according to the preferred embodiment, to produce death in the treated animals when administered as supplied, ad libitum for a period of 14 days.

Material and Methods

Test Animals:

Species: *Rattus norvegicus*

Strain: Sprague Dawley derived

Sex: Male and female (females nulliparous and non-pregnant)

Weight Range (at initiation): Male: 115–125 grams; Female: 115–125 grams

Number/Sex/Dose Level: 5 male, 5 female

Identification: Animals placed on test were identified with cage labels and ear punches.

Husbandry:

Diet: Standard laboratory feed for rodents, food and water were available ad libitum.

Housing: Animals were housed in suspended stainless steel wire-mesh cages in a room controlled for temperature (targeted at 21 degrees C±1 degree).

Acclimation: Animals were acclimated to the testing facility at least 7 days prior to the start of testing. Animals were observed for general health and suitability for testing during this period.

Justification of Selection of Test System: The rat is the preferred species for acute oral testing because of an extensive historical database.

Assignment to Dose Groups: Animals placed on test were randomly assigned to dose groups. Only rats with body weight within ±20% of the mean body weight of rats of the same age, strain, and sex were used.

Route of Administration: The test material was placed in 4 ounce, clear glass feeding jars for continuous ad libitum access to the food.

Frequency: Additional test material was added daily.

Test Duration: 7 days.

Dosing Procedure:

Animal Preparation: The rats were randomly selected and weighed on day 0, ear punched and single housed in cages.

Sample Preparation: The test material was dosed as supplied.

Treatment: An equal quantity of the test material was given to each animal.

In Life Observation

Body Weight: Body weight was recorded in grams for each animal daily.

Signs of Toxicity and Mortality: All test animals were observed for signs of toxicity and mortality twice daily seven days a week after administration. Test animals were observed for a total of 7 days after dosing. Observations included the following: circulatory, autonomic and central nervous systems, somatomotor activity, behavior patterns, skin and fur, and eyes and mucous membranes.

Post-Mortem Observations: A gross necropsy was performed on all test animals.

Results

Mortality: All animals died by day 7. On day 4, one female was found dead. On day 5, two males and one female were found dead. On day 6, two males and two females were found dead. On day 7, one male and one female were found dead.

Observations: Clinical observations noted during the study included dehydration, lethargy, diarrhea, tremors, weight loss, hunching and soft stool.

Body Weight: All animals had a daily weight loss.

Gross Pathology: At necropsy, tissue in some animals was autolyzed. Gross observations noted an absence of adipose tissue on test animals.

Discussion

Five male and five female Sprague Dawley derived rats for each dose were fed the sample as supplied.

All animals exhibited a daily weight loss and appeared dehydrated, however, they were noted to continue eating the test material during the daylight hours.

Conclusion

The test material, when administered as supplied cause death within 7 days to rats initially weighing between 115 to 125 grams.

EXAMPLE II

Toxicant-free pulverized corncobs prepared without the attractant and in a particulate form were distributed on ants, which died upon ingesting the sample.

EXAMPLE III

Eight tests on other materials having 1–4 day duration were conducted using the following materials prepared and dried in the particulate size of the preferred embodiment and dried to a level of 7%–9% moisture by weight:

| Testing 16 rats and 16 Mice | | | | | | | | | |
|---|---|---|---|---|---|---|---|---|---|
| Test No. | 1 | 2 | 3 | 4 | 5 | 6 | 7 | 8 | SPENT GRAIN |
| PERCENTAGE OF SPENT GRAIN IN EACH CELL | 100% | 10% |  | 5% | 25% | 15% | 20% |  | CORN |
|  |  | 5% | 20% | 10% |  | 5% |  | 40% | BARLEY |
|  |  | 5% | 5% |  |  | 30% |  | 10% | MILLET |
|  |  | 10% | 10% | 10% |  |  | 10% | 20% | RYE |
|  |  | 10% | 20% | 5% | 10% |  | 40% |  | OATS |
|  |  | 10% | 5% | 10% | 40% |  |  | 5% | RICE |
|  |  | 5% | 20% | 40% |  |  |  | 10% | SORGHUM |
|  |  | 40% | 20% | 5% | 15% |  | 30% | 10% | WHEAT |
|  |  | 5% |  | 15% | 10% | 50% |  | 5% | SOYBEAN |
|  | 100% | 100% | 100% | 100% | 100% | 100% | 100% | 100% |  |

All test animals died in 1–4 days. Attractants used included molasses, chocolate, blood plasma, beer, peanut butter and other similar materials.

Having described my invention, I claim:

1. A method for killing rodents which comprises orally administering to the rodents an effective amount of a food energy inhibitor consisting essentially of cellulose spent grain in a particulate form, mixed with an attractant, without the addition of a pesticide or poison.

2. A method as defined in claim 1, in which the cellulose spent rain is a crushed corncob.

3. A method as defined in claim 1, in which the cellulose spent grain is dried to a moisture content not exceeding 10% by weight.

4. A method of killing rodents, consisting essentially of an effective amount of a toxicant-free food energy inhibitor mixed with a toxicant-free rodent attractant for oral consumption by rodents, wherein said food energy inhibitor is an effective amount of particulate cellulose spent grain.

5. The method as defined in claim 4, in which the cellulose spent grain particles are bound together with the attractant in an extruded form.

6. The method as defined in claim 4, in which the cellulose spent grain particles are dried to a moisture content of no more than 10%.

7. The method as defined in claim 4, in which the cellulose spent grain comprises about 99% of the bait.

8. The method as defined in claim 4, in which the cellulose spent grain is crushed to a size that can be ingested by the rodent.

9. The method as defined in claim 4, in which the cellulose spent grain comprises a mixture ranging from 0–10% of the following spent grains: corncobs, oats, barley, rye, soybeans, millet, rice, wheat and sorghum, and the mixtures dried to a maximum moisture content not exceeding 10%.

10. A method for making a food energy inhibitor for rodents, comprising:
    milling grain to separate floury endosperm from the bran and germ;
    rolling the grain to extract oil from the germ to form a cellulose spent grain;
    drying and aerating the cellulose spent grain to a moisture content of less than 10%;
    mixing the cellulose spent grain with a toxicant-free binding substance and a toxicant-free rodent attractant;
    pelletizing the food energy inhibitor to a size suitable for ingestion by rodents; and drying the food energy inhibitor to a moisture level of 7% to 9%.

11. The method of claim 10, consisting essentially of forming a pellet for oral consumption by a rodent, wherein the toxicant-free cellulose spent grain particles are derived from the group consisting of corn cobs, peanut shells, hops, beet pulp, rice germ, rye, wheat, bagasse, bran, barley, whole oats/oat bran, and buckwheat, and mixtures thereof,
    and the toxicant-free attractant is selected from the group consisting of molasses, maple sugar, cottonseed meal, cane syrup, corn syrup, malt sugar, beet molasses, cane molasses, honey, bone meal, beer/ales, chocolate, peanut butter, beer, nuts, shrimp, fish, blood plasma, and mixtures thereof.

* * * * *